(12) United States Patent
Nishimura

(10) Patent No.: US 10,827,912 B2
(45) Date of Patent: Nov. 10, 2020

(54) STEREOSCOPIC ENDOSCOPE SYSTEM

(71) Applicant: OLYMPUS CORPORATION, Hachioji (JP)

(72) Inventor: Sayaka Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/698,871

(22) Filed: Nov. 27, 2019

(65) Prior Publication Data

US 2020/0093356 A1 Mar. 26, 2020

Related U.S. Application Data

(63) Continuation of application No. PCT/JP2018/016134, filed on Apr. 19, 2018.

(30) Foreign Application Priority Data

Jun. 6, 2017 (JP) ................. 2017-111793

(51) Int. Cl.
| | | |
|---|---|---|
| *A61B 1/00* | (2006.01) | |
| *H04N 13/239* | (2018.01) | |
| *G02B 9/64* | (2006.01) | |
| *G02B 13/18* | (2006.01) | |
| *H04N 7/18* | (2006.01) | |

(52) U.S. Cl.
CPC ........ *A61B 1/00193* (2013.01); *A61B 1/0005* (2013.01); *G02B 9/64* (2013.01); *G02B 13/18* (2013.01); *H04N 7/183* (2013.01); *H04N 13/239* (2018.05)

(58) Field of Classification Search
CPC .......................... A61B 1/0005; A61B 1/00193
See application file for complete search history.

(56) References Cited

U.S. PATENT DOCUMENTS

| | | | | |
|---|---|---|---|---|
| 5,776,049 A | * | 7/1998 | Takahashi | A61B 1/00193 600/111 |
| 5,860,912 A | * | 1/1999 | Chiba | A61B 1/00059 600/111 |

(Continued)

FOREIGN PATENT DOCUMENTS

| | | |
|---|---|---|
| JP | H07236610 A | 9/1995 |
| JP | 2013521941 A | 6/2013 |

(Continued)

OTHER PUBLICATIONS

International Preliminary Report on Patentability (IPRP) (and English language translation thereof) dated Dec. 10, 2019 issued in counterpart International Application No. PCT/JP2018/016134.

(Continued)

*Primary Examiner* — Rowina J Cattungal
(74) *Attorney, Agent, or Firm* — Holtz, Holtz & Volek PC

(57) ABSTRACT

A stereoscopic endoscope system includes:
a first objective optical system, a second objective optical system, an image sensor which has a first image pickup range corresponding to a range of a field of view of the first objective optical system and a second image pickup range corresponding to a range of a field of view of the second objective optical system; and a monitor, wherein the stereoscopic endoscope system satisfies the condition (1) and condition (2).

9 Claims, 4 Drawing Sheets

(56) References Cited

U.S. PATENT DOCUMENTS

| | | | |
|---|---|---|---|
| 10,105,034 B2 * | 10/2018 | Suga | .......... A61B 1/00096 |
| 2011/0228049 A1 * | 9/2011 | Kazakevich | ....... A61B 1/00009 |
| | | | 348/45 |
| 2017/0258297 A1 | 9/2017 | Suga | |

FOREIGN PATENT DOCUMENTS

| | | |
|---|---|---|
| JP | 2014028008 A | 2/2014 |
| JP | 6072392 B1 | 12/2015 |
| JP | 2016046780 A | 4/2016 |
| WO | 2011113062 A1 | 9/2011 |
| WO | 2016157623 A1 | 10/2016 |

OTHER PUBLICATIONS

International Search Report (ISR) dated Jun. 5, 2018 issued in International Application No. PCT/JP2018/016134.
Japanese Office Action dated Aug. 29, 2018 issued in counterpart Japanese Patent Application No. 2018-535442.
Written Opinion dated Jun. 5, 2018 issued in International Application No. PCT/JP2018/016134.

\* cited by examiner

STEREOSCOPIC ENDOSCOPE SYSTEM

CROSS-REFERENCE TO RELATED APPLICATION

The present application is a continuation application of PCT/JP2018/016134 filed on Apr. 19, 2018 which is based upon and claims the benefit of priority from Japanese Patent Application No. 2017-111793 filed on Jun. 6, 2017; the entire contents of which are incorporated herein by reference.

BACKGROUND

Technical Field

The present disclosure relates to a stereoscopic endoscope system.

Description of the Related Art

In recent years, in a medical field, to carry out an accurate and quick surgery of a lesion part, a surgical endoscope which enables stereoscopic observation has been treated as important. Particularly, in a field of surgery, an ability to observe a stereoscopic image safely and comfortably in a range of an observation distance of about 10 mm to 100 mm is necessary.

In order to carry out an accurate job, it is desirable to improve a resolution in a direction of depth. Moreover, in order to ease the job, it is desirable to reproduce a shape of a real object with fidelity on a 3-D (3-dimensional) monitor.

In a stereoscopic endoscope system in which two objective optical systems are built-in, in order to improve the resolution of the depth, it is necessary to increase a distance between optical axes of the two objective optical systems. Whereas for reproducing the shape of the object with fidelity, it is necessary to suppress a distortion in each objective optical system.

Stereoscopic visualization systems are disclosed in Japanese Patent No. 6072392 Publication (International Unexamined Patent Application Publication No. 2016-157623), Japanese Patent Application Laid-open Publication No. 2013-521941, Japanese Patent Application Laid-open Publication No. Hei 07-236610, and Japanese Patent Application Laid-open Publication No. 2014-028008.

SUMMARY

A stereoscopic endoscope system according to at least some embodiments of the present disclosure includes A stereoscopic endoscope system, comprising:
a first objective optical system;
a second objective optical system;
an image sensor which has a first image pickup range corresponding to a range of a field of view of the first objective optical system and a second image pickup range corresponding to a range of a field of view of the second objective optical system; and
a monitor, wherein
the stereoscopic endoscope system satisfies the following condition (1) and condition (2), where
condition (1) is a condition that a proportion of a first value which is obtained by multiplying a sum of a first distance and a second distance by a magnifying power of the monitor, and a vertical size T (mm) of a display screen of the monitor is larger than 1.5% and smaller than 10.5%, and
condition (2) is a condition that a proportion of a second value which is obtained by multiplying a difference between a third distance and a fourth distance by the magnifying power of the monitor, and the vertical size T of the display screen of the monitor is larger than 1.2% and smaller than 7.5%, where,
the first distance is a distance between a center of the first image pickup range and a position at which an image of a first object formed in the first image pickup range, the first object is disposed at an intermediate position in an optical axial distance between the first objective optical system and the second objective optical system at an observation distance 30 mm, and
the second distance is a distance between a center of the second image pickup range and a position at which an image of the first object is formed in the second image pickup range,
the third distance is a distance between the center of the first image pickup range and a position at which an image of a second object formed in the first image pickup range which is disposed at the farthest point in a direction of parallax at the observation distance 30 mm, and
the fourth distance is a distance between the center of the second image pickup range and a position at which an image of the second object is formed in the second image pickup range.

DETAILED DESCRIPTION

A stereoscopic endoscope system 100 according to an embodiment will be described below in detail with reference to the accompanying diagrams. However, the present disclosure is not restricted to the embodiment described below.

The stereoscopic endoscope system according to the present embodiment includes a first objective optical system, a second objective optical system, a first image sensor having an image pickup range corresponding to a range of a field of view of the first objective optical system, a second image sensor having an image pickup range corresponding to a range of a field of view of the second objective optical system, and a monitor, and satisfying the following condition (1) and condition (2), where, condition (1) is a condition that a proportion of a first value which is obtained by multiplying a sum of a first distance and a second distance by a magnifying power of the monitor, and a vertical size T (mm) of a display screen of the monitor is larger than 1.5% and smaller than 10.5%, and condition (2) is a condition that a proportion of a second value which is obtained by multiplying a difference between a third distance and a fourth distance by the magnification of monitor, and the vertical size T of the display screen of the monitor is larger than 1.2% and smaller than 7.5%, where the first distance is a distance between a center of an image pickup range on an image pickup surface of the first image sensor and a position at which an image of a first object which is at an intermediate position in an optical axial distance between the first objective optical system and the second objective optical system at an observation distance 30 mm is formed in the first image pickup range, and the second distance is a distance between a center of an image pickup range on an image pickup surface of the second image sensor and a position at which an image of the first object is formed on the second image sensor, the third distance is a distance between a center of the image pickup range on the image pickup surface of the first image sensor and a position at which an image of a second object which is at the farthest point in a direction of parallax at the observation distance 30 mm, is formed on the first image sensor, and the fourth distance is a distance between the center of the image pickup range on the image pickup surface of the second image sensor and a position at which an image of the second object is formed on the second image sensor.

Figure 1A:
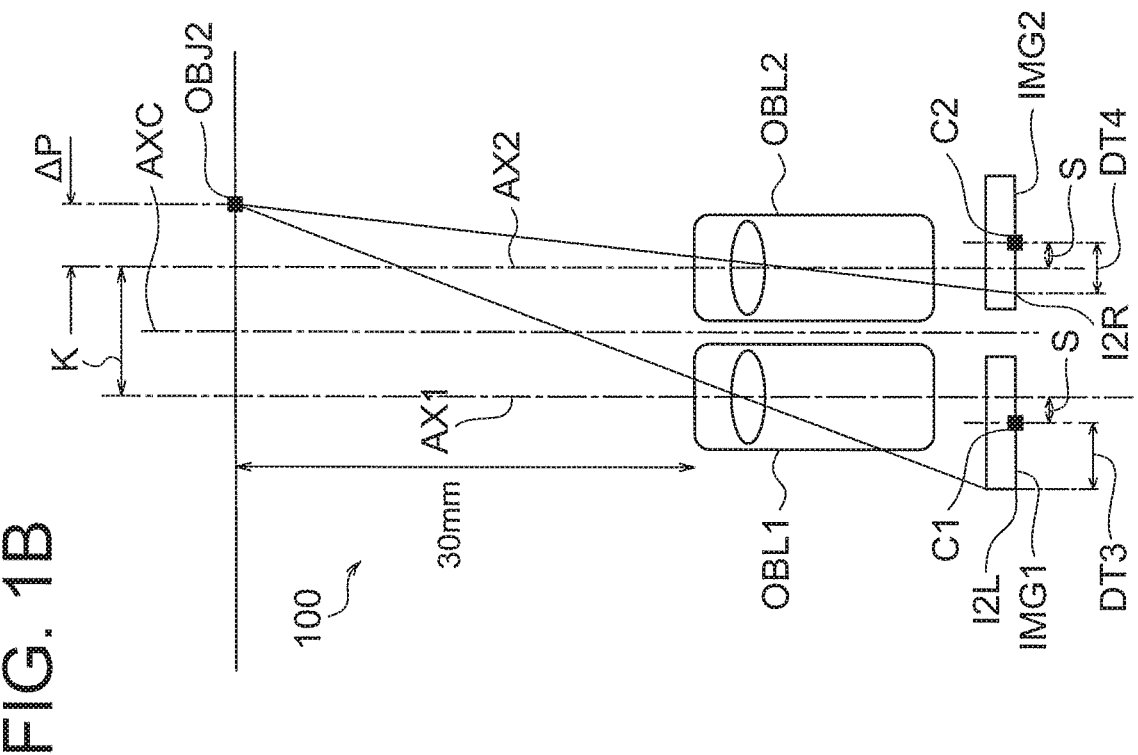
FIG. 1A is a schematic block diagram of a stereoscopic endoscope system according to an embodiment.
Figure 1B:
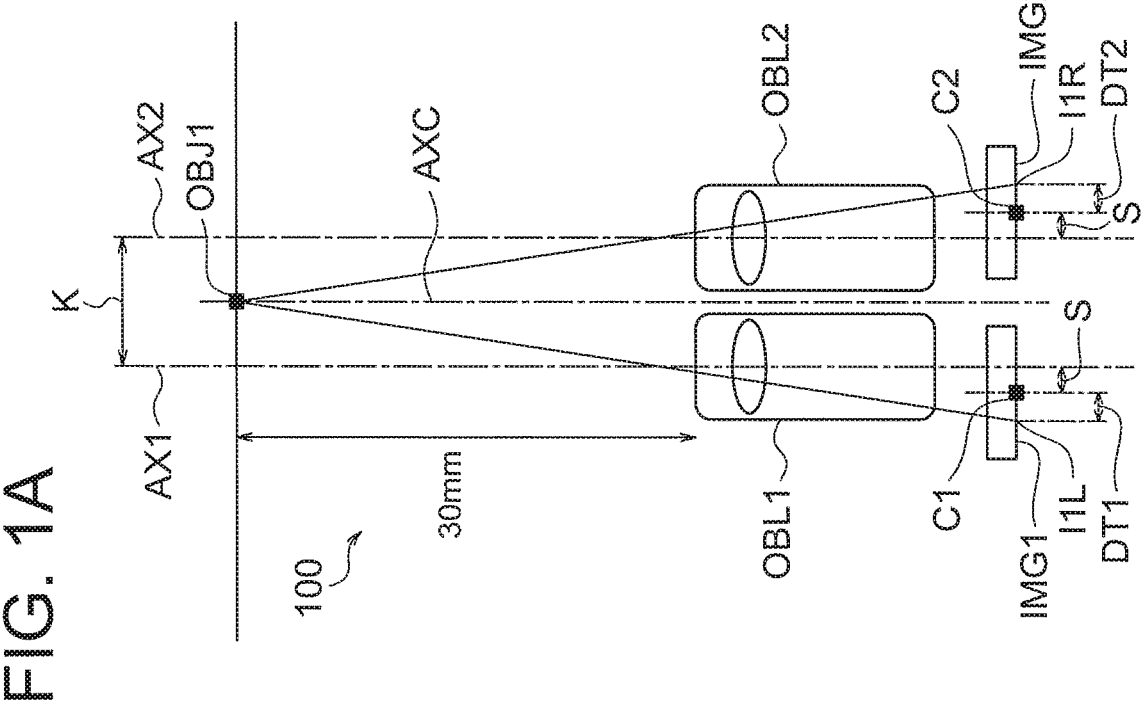
FIG. 1B is another schematic block diagram of the stereoscopic endoscope system according to the embodiment.
Figure 2A:
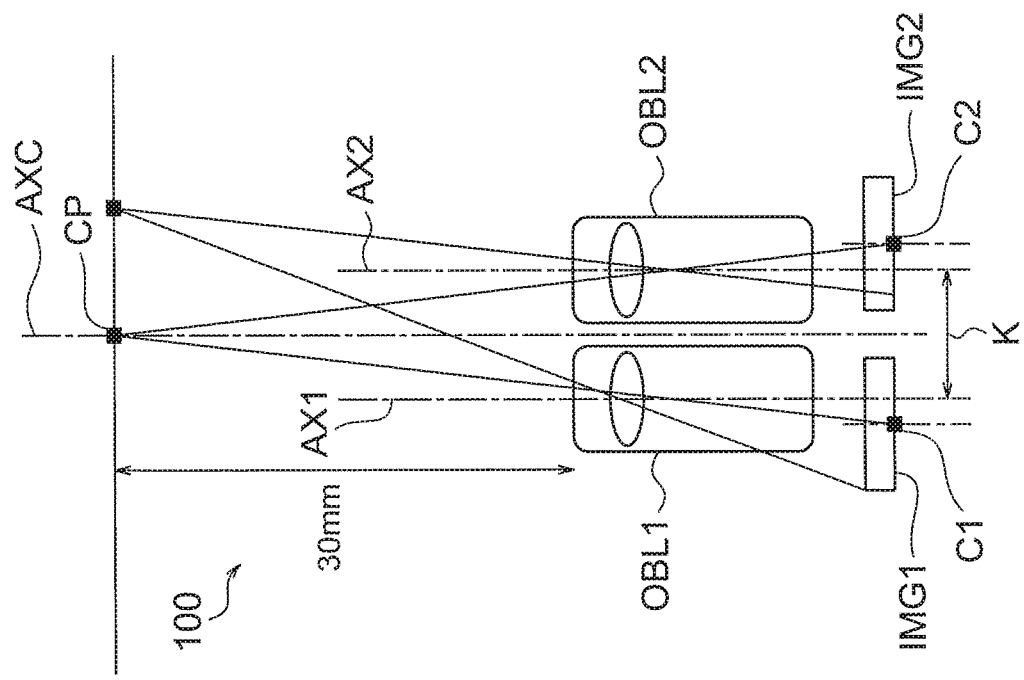
FIG. 2A is still another schematic block diagram of a stereoscopic endoscope system according to the embodiment.
Figure 2B:
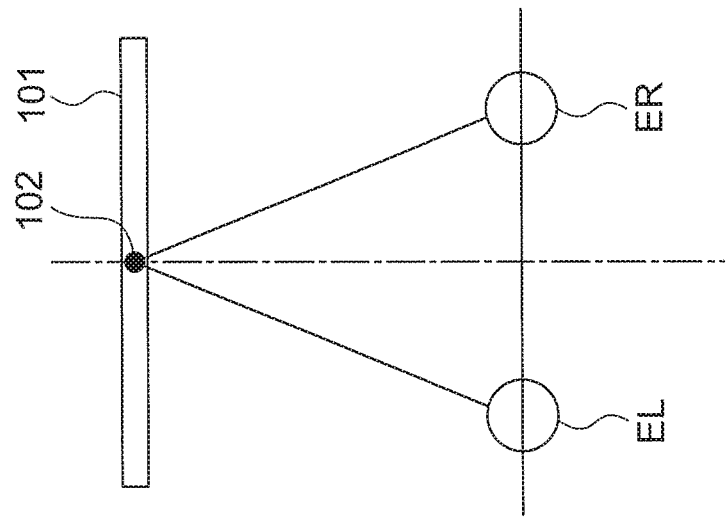
FIG. 2B is a diagram showing an arrangement at the time of reproducing an image picked up by the stereoscopic endoscope system of the present embodiment.

The present embodiment will be described by using FIG. 1A, FIG. 1B, FIG. 2A, and FIG. 2B. FIG. 1A is a schematic block diagram at the time of picking up an image of a first object OBJ1 by the stereoscopic endoscope system 100. FIG. 1B is another schematic block diagram at the time of picking up an image of a second object OBJ2 by the stereoscopic endoscope system 100. FIG. 2A is still another diagram of the stereoscopic endoscope system 100. FIG. 2B is diagram showing an arrangement at the time of reproducing an image picked up by the stereoscopic endoscope system 100.

To start with, the description will be made by using FIG. 1A, FIG. 1B, FIG. 2A, and FIG. 2B. The stereoscopic endoscope system 100 includes a first objective optical system OBL1 such as an objective optical system for left eye, and a second objective system OBL2 such as an objective optical system for right eye. A first image sensor IMG1 is disposed at a position of picking up an image corresponding to the first objective optical system OBL1. The second image sensor IMG2 is disposed at a position of picking up an image corresponding to the second objective optical system OBL2. Moreover, an image picked up is displayed on a monitor 101 shown in FIG. 2B.

The stereoscopic endoscope system 100 satisfies the following condition (1) and condition (2).

Condition (1) is a condition that a proportion of a first value which is obtained by multiplying a sum of a first distance DT1 and a second distance DT2 by a magnifying power, of the monitor 101 and a vertical size T of a display screen of the monitor 101 is larger than 1.5% and smaller than 10.5%.

Condition (2) is a condition that a proportion of a second value which is obtained by multiplying a difference between a third distance DT3 and a fourth distance DT4 by the magnifying power of the monitor 101 of the monitor 101 and the vertical size T of the display screen of the monitor 101 is larger than 1.2% and smaller than 7.5%.

The first distance DT1 is a distance between a center C1 of an image pickup range on an image pickup surface of the image sensor IMG1 and a position I1L at which an image of a first object OBJ1 which is at an intermediate position of a distance between optical axes AX1 and AX2 of the first objective optical system OBL1 and the second objective optical system OBL2 at the observation distance 30 mm, is formed on the first image sensor IMG1. In FIG. 1A, the middle of the optical axes AX1 and AX2 is indicated by an axis AXC.

The second distance DT2 is a distance between a center C2 of an image pickup range on an image pickup surface of the second image sensor IMG2 and a position I1R at which an image of the first object OBJ1 is formed on the second image sensor IMG2.

The third distance DT3 is a distance between the center C1 of the image pickup range on the image pickup surface of the first image sensor IMG1 and a position I2L at which an image of a second object OBJ2 which is at the farthest point in a direction of parallax of a range of a field of view of any one of the first image sensor IMG1 and the second image sensor IMG2 at the observation distance 30 mm, is formed on the first image sensor IMG1.

The fourth distance DT4 is a distance between the center of the image pickup range on the image pickup surface of the second image sensor IMG2 and a position at which an image of the second object OBJ2 is formed on the second image sensor IMG2.

The first object OBJ1 and the second object OBJ2 are in a central area and a peripheral area respectively of an observation field. Here, the peripheral area is the most peripheral area in a direction in which the parallax has occurred.

According to a combination of distortion and axial distance, characteristics of popping out of image and rising of image are determined. By satisfying conditions (1) and (2), it is possible to balance appropriately the popping out and rising of image. Accordingly, it is possible to achieve a natural stereoscopic effect.

In the present embodiment, a first value Hc is indicated by the following condition (A).

$$Hc=(2\times M\times\beta\times(K/2)\times(Dc+1)-2S\times M\times\beta)/T \qquad (A)$$

where,

M denotes the magnifying power ($=(x'/x)\times(Im/Ip)$) of the monitor 101, x' denotes the number of pixels of the monitor 101, x denotes the number of pixels of the first objective optical system OBL1 and the second objective optical system OBL2, Im denotes a pixel pitch of the monitor 101, Ip denotes a pixel pitch of either the first image sensor IMG1 or the second image sensor IMG2, β denotes a magnifying power of the first objective optical system OBL1 and the second objective optical system OBL2, moreover, K denotes a distance between the optical axes AX1 and AX2 of the first objective optical system OBL1 and the second objective optical system OBL2, and K may be a distance between a pupil of the first objective optical system OBL1 and a pupil of the second objective optical system OBL2, or, a distance in an opening portion of the first objective optical system OBL1 and an opening portion of the second objective optical system OBL2.

T denotes a vertical size of the monitor.

Moreover, the number of pixels may be any of the number of pixels in the direction of parallax and the number of pixels in a diagonal direction of the image sensor.

Dc denotes an amount of distortion (%) when an image of the first object OBJ1 is formed on the first image sensor IMG1 and the second image sensor IMG2, or in other words, an amount of distortion (%) at a position at which an image of the object OBJ1 which is at the center of the range of the field of view, is formed, and S denotes a distance between the center C1 of the image pickup range on the image pickup surface of the first image sensor IMG1 and the optical axis AX1 of the first objective optical system OBL1, or a distance between the center C2 of the image pickup range on the image pickup surface of the second image sensor IMG2 and the optical axis AX2 of the second objective optical system OBL2.

Condition (A) is a condition which regulates controlling the popping out of an object at the center of the field of view by the optical axial distance K.

When the first value Hc falls below a lower limit value of condition (A), a depth resolution becomes low. When the first value Hc exceeds an upper limit value of condition (A), popping out of an object in a central area of the field of view becomes excessive, and it is not possible to carry out stereoscopic vision comfortably.

In the present embodiment, a second value Hs is indicated by the following condition (B).

$$Hs=(M\times\beta\times((\Delta P+K)\times(D+1)-\Delta P\times(D'+1)-2S))/T \quad (B)$$

where,

M denotes the magnifying power $(=(x'/x)\times(Im/Ip))$, x' denotes the number of pixels of the monitor 101, x denotes the number of pixels of the first objective optical system OBL1 and the second objective optical system OBL2, Im denotes the pixel pitch of the monitor 101, Ip denotes the pixel pitch of either the first image sensor IMG1 or the second image sensor IMG2, β denotes a magnifying power of the first objective optical system OBL1 and the second objective optical system OBL2, ΔP denotes a difference between the maximum length in a range of the field of view in a direction perpendicular to the optical axes AX1 or AX2 of the first objective optical system OBL1 or the second objective optical system OBL2, and the optical axial distance, K denotes a distance between the optical axes AX1 and AX2 of the first objective optical system OBL1 and the second objective optical system OBL2, D denotes an amount of distortion (%) when an image of the second object OBJ2 is formed on the first image sensor IMG1, D' denotes an amount of distortion (%) when an image of the second object OBJ2 is formed on the second image sensor IMG2, S denotes the distance between the center C1 of the image pickup range on the image pickup surface of the first image sensor IMG1 and the optical axis AX1 of the first objective optical system OBL1, or a distance between the center C2 of the image pickup range on the image pickup surface of the second image sensor IMG2 and the optical axis AX2 of the second objective optical system OBL2.

Condition (B) is a condition which regulates controlling the popping out of an object in a peripheral area of the field of view by the optical axial distance and the distortion, and controlling popping out of a forceps in a periphery of the field of view at the time of near-point observation by the distortion. Moreover, condition (B) is a condition for regulating controlling popping out of an object at a center of the field of view by the optical axial distance K.

When the second value Hs falls below a lower limit value of condition (B), popping of the forceps in the peripheral area at the time of near-point observation becomes large. Moreover, when the second value exceeds an upper limit value of condition (B), a shape different from the actual shape is reproduced when a flat object is observed.

Moreover, according to a preferable aspect of the present embodiment, it is desirable to determine condition (1) by varying appropriately the distance between the optical axes AX1 and AX2.

Furthermore, according to a preferable aspect of the present embodiment, it is desirable to determine condition (2) by varying appropriately the amount of distortion when an image of the second object OBJ2 is formed on the first image sensor IMG1 and the second image sensor IMG2.

According to a preferable aspect of the present embodiment, it is desirable that in condition (1), the optical axial distance K is not less than 2 mm and not more than 6 mm. Accordingly, it is possible to improve further the depth resolution, and to suppress the popping out of an object in the central area.

Moreover, according to a preferable aspect of the present embodiment, it is desirable that in condition (2), the amount of distortion D is not less than −30% and not more than −10%. Accordingly, it is possible to generate distortion deliberately, and to suppress the popping out of image in the peripheral area of the field of view and popping out of the forceps in the periphery of the field of view at the time of near-point observation.

Furthermore, according to a preferable aspect of the present embodiment, it is desirable that the second value Hs which is obtained by multiplying a difference between the third distance DT3 and the fourth distance DT4 by the magnifying power of the monitor 101 is not less than 1.8% and not more than 7.2%, and the amount of distortion D is not less than −22% and not more than −10%. Accordingly, by reducing the amount of distortion, it is possible to reduce a vertical shift in a left image and a right image due to distortion of a distorted image.

According to a preferable aspect of the present embodiment, it is desirable that an observation distance at which a center point of an image displayed on the monitor 101 assumes zero parallax is not more than 40 mm.

This signifies that a cross point CP on the optical axis AXC shown in FIG. 2A is at a distance not more than 40 mm. Moreover, the 'zero parallax' means that a center point 102 of a reproduced image is on a surface of the monitor 101 (refer to FIG. 2B). An observer observes the monitor 101 in a range of 80 cm to 2 m.

Even in a case in which the cross point CP is at a distance not more than 40 mm, at the time of normal observation (far-point observation), an arrangement of the stereoscopic endoscope system is to be set such that it is not diverged.

Examples will be described below.

Figure 3A:
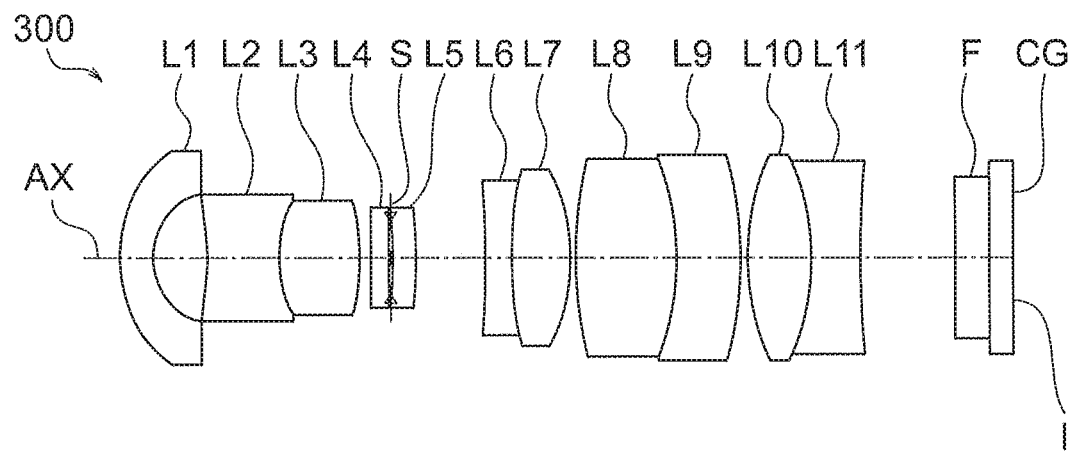
FIG. 3A is a lens cross-sectional view at the time of normal observation of a stereoscopic endoscope system according to an example 1.
Figure 3B:
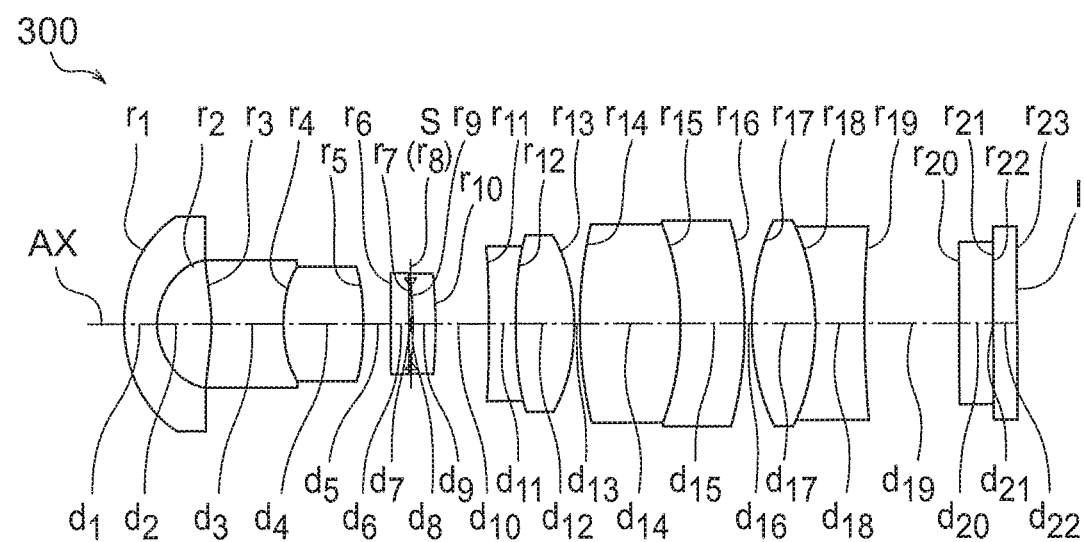
FIG. 3B is a lens cross-sectional view at the time of near-point observation of the stereoscopic endoscope system according to the example 1.

FIG. 3A is a lens cross-sectional view at the time of normal observation of a stereoscopic endoscope system 300 according to an example 1. FIG. 3B is a lens cross-sectional view at the time of near-point observation (magnified observation) of the stereoscopic endoscope system 300 according to the example 1. In the present example, −10% distortion is generated.

The stereoscopic endoscope system 300 of the example 1 includes in order from an object side, a negative meniscus lens L1 having a convex surface directed toward the object side, a biconcave negative lens L2, a biconvex positive lens L3, a plane parallel plate (infrared absorbing filter) L4, an aperture stop S, a positive meniscus lens L5 having a convex surface directed toward an image side, a biconcave negative lens L6, a biconvex positive lens L7, a biconvex positive lens L8, a negative meniscus lens L9 having a convex surface directed toward the image side, a biconvex positive lens L10, a biconcave negative lens L11, a cover glass F, and a CCD (charge couple device) cover glass CG.

The biconcave negative lens L2 and the biconvex positive lens L3 are cemented. The biconcave negative lens L6 and the biconvex positive lens L7 are cemented. The biconvex positive lens L8 and the negative meniscus lens L9 having a convex surface directed toward the image side are cemented. The biconvex positive lens L1 and the biconcave negative lens L11 are cemented.

The cover glass F and the CCD cover glass CG are cemented. Here, d21 is an adhesive layer. Moreover, YAG (yttrium aluminum garnet) laser cut coating is applied to an object side of the infrared absorbing filter L4 and an LD laser cut coating is applied to an image side of the infrared absorbing filter L4.

The normal observation and the near-point (magnified) observation are carried out by moving the plane parallel plate L4, the aperture stop S, and the positive meniscus lens L5 integrally toward the image side.

Example 2

Figure 4A:
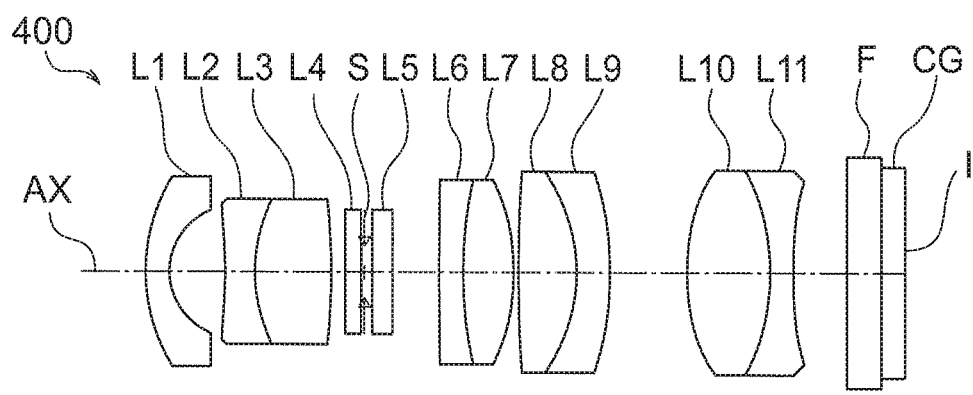
FIG. 4A is a lens cross-sectional view at the time of normal observation of a stereoscopic endoscope system according to an example 2.
Figure 4B:
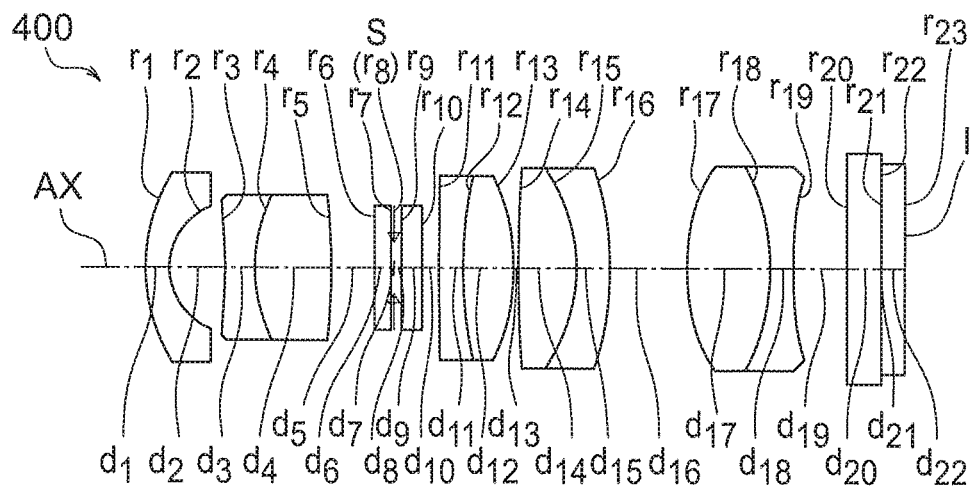
FIG. 4B is a lens cross-sectional view at the time of near-point observation of the stereoscopic endoscope system according to the example 2.

FIG. 4A is a lens cross-sectional view at the time of normal observation of a stereoscopic endoscope system 400 according to an example 2. FIG. 4B is a lens cross-sectional view at the time of near-point observation of the stereoscopic endoscope system 400 according to the example 2. In the present example, −16% distortion is generated.

The stereoscopic endoscope system 400 of the example 2 includes in order from an object side, a negative meniscus lens L1 having a convex surface directed toward the object side, a biconcave negative lens L2, a biconvex positive lens L3, a plane parallel plate (infrared absorbing filter) L4, an aperture stop S, a planoconvex positive lens L5 having a flat surface directed toward the object side, a planoconcave negative lens L6 having a flat surface directed toward the object side, a biconvex positive lens L7, a biconvex positive lens L8, a negative meniscus lens L9 having a convex surface directed toward an image side, a biconvex positive lens L10, a biconcave negative lens L11, a cover glass F, and a CCD cover glass CG.

The biconcave negative lens L2 and the biconvex positive lens L3 are cemented. The planoconcave negative lens L6 and the biconvex positive lens L7 are cemented. The biconvex positive lens L8 and the negative meniscus lens L9 having a convex surface directed toward the image side are cemented. The biconvex positive lens L10 and the biconcave negative lens L11 are cemented.

The cover glass F and the CCD cover glass CG are cemented. Here, d21 is an adhesive layer. Moreover, YAG laser cut coating is applied to an object side of the infrared absorbing filter L4 and an LD laser cut coating is applied to an image side of the infrared absorbing filter L4.

The normal observation and the near-point (magnified) observation are carried out by moving the plane parallel plate L4, the aperture stop S, and the planoconvex positive lens L5 integrally toward the image side.

Numerical data for each embodiment is shown below. With regard to symbols, r denotes a radius of curvature of each lens surface, d denotes a distance between two lens surfaces, ne denotes a refractive index for an e-line of each lens, ve denotes Abbe's number for each lens, * mark denotes an aspheric surface, and stop is an aperture stop.

Moreover, when an optical axial direction is z, a direction orthogonal to the optical axis is y, a conical coefficient is k, and aspherical coefficients are A4, A6, A8, and A10, an aspheric surface shape is indicated by the following expression.

$$z=(y^2/r)/[1+\{1-(1+k)(y/r)^2\}^{1/2}]+A4y^4+A6y^6+A8y^8+A10y^{10}$$

Moreover, for the aspherical coefficients, 'E$^{-n}$' (n is an integer) indicates '10$^{-n}$'.

Symbols for various basic values are common in the numerical data of examples.

Example 1

| Unit mm | | | | |
|---|---|---|---|---|
| Surface data | | | | |
| Surface no. | r | d | ne | ve |
| Object plane | ∞ | 43.4151 | 1 | |
| 1 | 2.3823 | 0.3949 | 1.81078 | 40.92 |
| 2 | 0.9151 | 0.6777 | 1 | |
| 3 | −5.5508 | 0.8934 | 1.88815 | 40.76 |
| 4 | 1.9264 | 0.9687 | 1.76167 | 27.51 |
| 5 | −4.397 | 0.1565 Variable | 1 | |
| 6 | ∞ | 0.2235 | 1.523 | 65.13 |
| 7 | ∞ | 0.0284 | 1 | |
| 8 (Stop) | ∞ | 0 | 1 | |
| 9 | −9.5812 | 0.2981 | 1.65425 | 58.55 |
| 10 | −7.5594 | 0.849 Variable | 1 | |
| 11 | −26.843 | 0.3181 | 1.93429 | 18.9 |
| 12 | 5.4361 | 0.747 | 1.67765 | 32.1 |
| 13 | −2.6970 | 0.0656 | 1 | |
| 14 | 7.2754 | 1.2102 | 1.74795 | 44.78 |
| 15 | −4.2565 | 0.8066 | 1.93429 | 18.9 |
| 16 | −5.1872 | 0.0745 | 1 | |
| 17 | 3.3362 | 0.7915 | 1.59143 | 61.14 |
| 18 | −3.5799 | 0.5961 | 1.93429 | 18.9 |
| 19 | 19.0140 | 1.1782 | 1 | |
| 20 | ∞ | 0.3726 | 1.51825 | 64.14 |
| 21 | ∞ | 0.0149 | 1.5119 | 64.05 |
| 22 | ∞ | 0.2981 | 1.507 | 63.26 |
| Image plane | ∞ | 0 | | |

| Aspherical surface data |
|---|
| 1st surface |
| k = 0 |
| A2 = 0.00E+00, A4 = 5.3715E−02, A6 = −3.4719E−03, |
| A8 = 8.1102E−04 |
| 2nd surface |
| k = 0 |
| A2 = 0.00E+00, A4 = 8.0179E−02, A6 = 2.3258E−02, |
| A8 = 6.6214E−02 |

| Various data | | |
|---|---|---|
| | Normal observation state | Magnified observation state |
| Object distance | 43.41506 | 32.19677 |
| d5 | 0.15648 | 0.33562 |
| d10 | 0.849 | 0.66986 |

1st value Hc = 9.8%
2nd value Hs = 7.15%

Example 2

Unit mm

Surface data

| Surface no. | r | d | ne | ve |
|---|---|---|---|---|
| Object plane | ∞ | 60.0000 | 1 | |
| 1* | 2.9142 | 0.4 | 1.81078 | 40.88 |
| 2* | 1.0606 | 0.84 | 1 | |
| 3 | −18.377 | 0.5 | 2.01169 | 28.27 |
| 4 | 2.634 | 1.2 | 1.85504 | 23.78 |
| 5 | −8.532 | 0.21 Variable | 1 | |
| 6 | ∞ | 0.3 | 1.523 | 65.13 |
| 7 | ∞ | 0.03 | 1 | |
| 8 (Stop) | ∞ | 0.11 | 1 | |
| 9 | ∞ | 0.35 | 1.65425 | 58.55 |
| 10 | −35.645 | 0.72 Variable | 1 | |
| 11 | ∞ | 0.4 | 2.01169 | 28.27 |
| 12 | 9.972 | 0.78 | 1.80642 | 34.97 |
| 13 | −3.375 | 0.08 | 1 | |
| 14 | 24.688 | 0.9 | 1.73234 | 54.68 |
| 15 | −2.782 | 0.53 | 1.93429 | 18.9 |
| 16 | −5.625 | 1.2453 | 1 | |
| 17 | 3.375 | 1.3 | 1.73234 | 54.68 |
| 18 | −3.375 | 0.35 | 2.01169 | 28.27 |
| 19 | 8.042 | 0.856 | 1 | |
| 20 | ∞ | 0.5 | 1.51825 | 64.14 |
| 21 | ∞ | 0.02 | 1.5119 | 64.05 |
| 22 | ∞ | 0.4 | 1.507 | 63.26 |
| Image plane | ∞ | 0 | | |

Aspherical surface data

1st surface k = 0.8038
A2 = 0.00E+00, A4 = 7.55E−04, A6 = 5.60E−04,
A8 = −1.86E−04

2nd surface k = −0.1138
A2 = 0.00E+00, A4 = 2.51E−03, A6 = −7.25E−04,
A8 = 4.59E−03

Various data

| | Normal observation state | Magnified observation state |
|---|---|---|
| Object distance | 60 | 30 |
| d5 | 0.21 | 0.68 |
| d10 | 0.72 | 0.25 |

1st value of Hc = 7.77%
2nd value Hs = 4.71%

The abovementioned stereoscopic endoscope system may satisfy the plurality of arrangements simultaneously. Doing so is preferable for achieving a favorable stereoscopic endoscope system. Moreover, a combination of preferable arrangements is arbitrary. Furthermore, regarding the conditions, an upper limit value or a lower limit value of further restricted numerical range of condition may be restricted.

Various embodiments of the present disclosure have been described heretofore. However, the present disclosure is not restricted to the embodiments described heretofore, and embodiments in which the arrangements of the abovementioned embodiments are combined appropriately without departing from the scope of the disclosure are also within the scope of the present disclosure.

As described heretofore, the present disclosure is useful for a stereoscopic endoscope system which has a high resolution in the direction of depth, and which enables a favorable stereoscopic vision without an object in a central portion and an object in a peripheral portion popping out inappropriately, while reproducing the shape of the object appropriately.

The present disclosure shows an effect that it is possible to provide a stereoscopic endoscope system which has a high resolution in the direction of depth, and which enables a favorable stereoscopic vision without an object in a central portion and an object in a peripheral portion popping out inappropriately, while reproducing the shape of the object appropriately.

What is claimed is:

1. A stereoscopic endoscope system, comprising:
a first objective optical system;
a second objective optical system;
an image sensor which has a first image pickup range corresponding to a range of a field of view of the first objective optical system and a second image pickup range corresponding to a range of a field of view of the second objective optical system; and
a monitor, wherein
the stereoscopic endoscope system satisfies the following condition (1) and condition (2), where
condition (1) is a condition that a proportion of a first value which is obtained by multiplying a sum of a first distance and a second distance by a magnifying power of the monitor, and a vertical size T (mm) of a display screen of the monitor is larger than 1.5% and smaller than 10.5%, and
condition (2) is a condition that a proportion of a second value which is obtained by multiplying a difference between a third distance and a fourth distance by the magnifying power of the monitor, and the vertical size T of the display screen of the monitor is larger than 1.2% and smaller than 7.5%, where,
the first distance is a distance between a center of the first image pickup range and a position at which an image of a first object formed in the first image pickup range, the first object is disposed at an intermediate position in an optical axial distance between the first objective optical system and the second objective optical system at an observation distance 30 mm, and
the second distance is a distance between a center of the second image pickup range and a position at which an image of the first object is formed in the second image pickup range,
the third distance is a distance between the center of the first image pickup range and a position at which an image of a second object formed in the first image pickup range which is disposed at the farthest point in a direction of parallax at the observation distance 30 mm, and
the fourth distance is a distance between the center of the second image pickup range and a position at which an image of the second object is formed in the second image pickup range.

2. The stereoscopic endoscope system according to claim 1, wherein the first value is indicated by the following expression (A)

$$(2 \times M \times \beta \times (K/2) \times (Dc+1) - 2S \times M \times \beta) \quad (A)$$

where,
M denotes the magnifying power of the monitor,
β denotes a magnifying power of the first objective optical system and the second objective optical system,
K denotes an optical axial distance between the first objective optical system and the second objective optical system, Dc denotes an amount of distortion when an image of the first object is formed in the first image pickup range and the second image pickup range, and S denotes one of a distance between the center of the first image pickup range and an optical axis of the first objective optical system, or a distance between the center of the second image pickup range and an optical axis of the second objective optical system.

3. The stereoscopic endoscope system according to claim 1, wherein the second value is indicated by the following expression (B)

$$(M \times \beta \times ((\Delta P + K) \times (D+1) - \Delta P \times (D'+1) - 2S)) \quad \text{(B)}$$

where,

M denotes the magnifying power of the monitor,

β denotes the magnifying power of the first objective optical system and the second objective optical system, ΔP denotes a difference between the maximum length in a range of a field of view in a direction perpendicular to an optical axis of the first objective optical system, or the second objective optical system and an optical axial distance, K denotes an optical axial distance between the first objective optical system and the second objective optical system, D denotes an amount of distortion when an image of the second object is formed in the first image pickup range, D' denotes an amount of distortion when an image of the second object is formed in the second image pickup range, and S denotes one of a distance between the center of the first image pickup range and an optical axis of the first objective optical system, or a distance between the center of the second image pickup range and an optical axis of the second objective optical system.

4. The stereoscopic endoscope system according to claim 3, wherein in condition (2), the amount of distortion when the image of the second object is formed in the first image pickup range is not less than −30% and not more than −10%.

5. The stereoscopic endoscope system according to claim 3, wherein the second value is not less than 1.8% and not more than 7.2%, and the amount of distortion when an image of the second object is formed in the first image pickup range is not less than −22% and not more than −10%.

6. The stereoscopic endoscope system according to claim 3, wherein the second value is not less than 1.8% and not more than 4.71%, and the amount of distortion when an image of the second object is formed on the first image pickup range is not less than −16% and not more than −10%.

7. The stereoscopic endoscope system according to claim 1, wherein in condition (1), the optical axial distance is not less than 2 mm and not more than 6 mm.

8. The stereoscopic endoscope system according to claim 1, wherein an observation distance at which a center point of an image displayed on the monitor assumes zero parallax is not more than 40 mm.

9. The stereoscopic endoscope system according to claim 1, wherein the image sensor includes a first image sensor having the first image pickup range and a second image sensor having the second image pickup range.

* * * * *